US005534197A

United States Patent [19]
Scheibel et al.

[11] Patent Number: 5,534,197
[45] Date of Patent: Jul. 9, 1996

[54] GEMINI POLYHYDROXY FATTY ACID AMIDES

[75] Inventors: Jeffrey J. Scheibel; Daniel S. Connor; Yi-Chang Fu, all of Cincinnati, Ohio

[73] Assignee: The Procter & Gamble Company, Cincinnati, Ohio

[21] Appl. No.: 342,558

[22] Filed: Nov. 21, 1994

Related U.S. Application Data

[63] Continuation-in-part of Ser. No. 187,251, Jan. 25, 1994, abandoned.

[51] Int. Cl.$^6$ .................... C07C 233/18; C07C 233/36; C11D 1/52
[52] U.S. Cl. ............... 510/356; 554/56; 564/159; 134/42; 510/502; 510/126; 510/130; 510/433; 510/423; 510/237; 510/341; 510/306; 510/350; 510/308; 510/294; 510/349
[58] Field of Search .................... 252/544, 546, 252/548, 525, 527, 529, 8.8; 564/159; 134/42

[56] References Cited

U.S. PATENT DOCUMENTS

| | | | |
|---|---|---|---|
| 2,703,798 | 3/1955 | Schwartz | 260/211 |
| 3,214,475 | 10/1965 | Butter | 260/606 |
| 3,454,647 | 7/1969 | Kersnar et al. | 260/584 |
| 3,637,495 | 1/1972 | Eckert et al. | 252/8.8 |
| 3,654,166 | 4/1972 | Eckert et al. | 252/117 |
| 4,021,539 | 5/1977 | Moller et al. | 424/73 |
| 4,049,557 | 9/1977 | Wixon | 252/8.8 |
| 4,255,294 | 3/1981 | Rudy et al. | 252/524 |
| 5,174,927 | 12/1992 | Honsa | 252/543 |
| 5,188,769 | 2/1993 | Connor et al. | 252/548 |
| 5,194,639 | 3/1993 | Connor et al. | 554/66 |
| 5,223,179 | 6/1993 | Connor et al. | 252/548 |
| 5,236,615 | 8/1993 | Trinh et al. | 252/174.11 |
| 5,248,333 | 9/1993 | Worschech et al. | 106/38.24 |

FOREIGN PATENT DOCUMENTS

| | | | |
|---|---|---|---|
| 164072 | 12/1985 | European Pat. Off. | C11D 1/20 |
| 258500 | 3/1988 | European Pat. Off. | C11D 3/12 |
| 385452 | 9/1990 | European Pat. Off. | C07C 235/80 |
| 390986 | 10/1990 | European Pat. Off. | C11D 1/52 |
| 398101 | 11/1990 | European Pat. Off. | C07C 237/06 |
| 1360018 | 3/1964 | France . | |
| 1411715 | 6/1964 | France . | |
| 1261861 | 2/1968 | Germany . | |
| 60-096695 | 5/1985 | Japan . | |
| 3-246265 | 11/1991 | Japan | C07C 233/18 |
| 2203177 | 10/1988 | United Kingdom | D06M 13/40 |
| WO90/14332 | 11/1990 | WIPO | C07C 231/02 |
| WO92/00272 | 1/1992 | WIPO | C07C 233/38 |
| WO92/06171 | 4/1992 | WIPO | C11D 17/00 |
| WO92/06150 | 4/1992 | WIPO | C11D 3/00 |
| WO92/05764 | 4/1992 | WIPO | A61K 7/06 |
| WO92/06151 | 4/1992 | WIPO | C11D 1/52 |
| WO92/15554 | 9/1992 | WIPO | C07C 233/18 |
| WO93/06148 | 4/1993 | WIPO | C08G 63/20 |

OTHER PUBLICATIONS

Badoiu, Letitia M. et al., Abstract No. 200335, Chemical Abstracts, vol. 107, No. 22 (Nov. 30, 1987), "Textile softeners based on alkoxymethyl derivatives of fatty amides", p. 100.

Pfannemuller, Beate and Welte, Wolfram, "Amphiphilic Properties of Synthetic Glycolipids Based on Amide Linkages. I. Electron Microscopic Studies on Aqueous Gels", *Chemistry and Physics of Lipids*, 37 #3 (1985) 227–240.

Zhu, Yun–peng; Masuyama, Araki; Kirito, Yoh–ichi; Okahara, Mitsuo and Rosen, Milton J., "Preparation and Properties of Glycerol–Based Double– or Triple–Chain Surfactants with Two Hydrophilic Ionic Groups", *JAOCS*, vol. 69, No. 7 (Jul. 1992), pp. 626–632.

*Primary Examiner*—Paul Lieberman
*Assistant Examiner*—Lorna M. Douyon
*Attorney, Agent, or Firm*—J. C. Rasser; J. J. Yetter; K. W. Zerby

[57] ABSTRACT

Gemini polyhydroxy fatty acid amide compounds and laundry, cleaning, fabric and personal care compositions comprising these compounds.

9 Claims, No Drawings

GEMINI POLYHYDROXY FATTY ACID AMIDES

This is a continuation-in-part application of pending application U.S. Ser. No. 08/187,251, filed Jan. 25, 1994 now abandoned.

TECHNICAL FIELD

The present invention relates to gemini polyhydroxy fatty acid amide compounds. This invention also relates to laundry, cleaning, fabric and personal care compositions comprising these compounds.

BACKGROUND OF THE INVENTION

The formulation of detergent compositions presents a considerable challenge, since effective compositions are required to remove a variety of soils and stains from diverse substrates. In particular, the removal of greasy/oily soils quickly and efficiently can be problematic. While a review of the literature would seem to indicate that a wide selection of surfactants is available to the detergent manufacturer, the reality is that many such materials are specialty chemicals which are not suitable in low unit cost items such as home-use detergent compositions. The fact remains that most home-use detergents still comprise one or more of the conventional ethoxylated nonionic and sulfated or sulfonated anionic surfactants, presumably due to economic considerations.

The challenge to the detergent manufacturer seeking improved fabric cleaning has been increased by various environmental factors. For example, some nonbiodegradable ingredients have fallen into disfavor. Effective phosphate builders have been banned by legislation in many countries. Moreover, many surfactants are often available only from nonrenewable resources such as petrochemicals. Accordingly, the detergent manufacturer is quite limited in the selection of surfactants which are effective cleaners, biodegradable and, to the extent possible, available from renewable resources such as natural fats and oils, rather than petrochemicals.

Considerable attention has lately been directed to nonionic surfactants which can be prepared using mainly renewable resources, such as fatty esters and sugars. One such class of surfactants includes the N-alkyl polyhydroxy fatty acid amides. Moreover, the combination of such nonionic surfactants with conventional anionic surfactants such as the alkyl sulfates, alkyl benzene sulfonates, alkyl ether sulfates, and the like has also been studied. Indeed, substantial success in the formulation of dishwashing compositions has recently been achieved using the N-alkyl polyhydroxy fatty acid amides. However, even these superior surfactants do suffer from some drawbacks. For example, their solubility is not as high as might be desired for optimal formulations and this is exacerbated at chain lengths of about $C_{16}$ and above. At high concentrations in water they can be difficult to handle and pump, so additives must be employed in manufacturing plants to control their viscosity. While quite compatible with anionic surfactants, their compatibility can be diminished substantially in the presence of water hardness cations. And, of course, there is always the objective to find new surfactants which lower interfacial tensions to an even greater degree than the N-alkyl polyhydroxy fatty acid amides at low temperatures in order to increase cleaning performance.

The present invention gemini polyhydroxy fatty acid amide compounds have been found to be versatile materials useful in a variety of cleaning compositions, especially as surfactants for use therein.

BACKGROUND ART

Japanese Kokai HEI 3[1991]-246265 Osamu Tachizawa, U.S. Pat. Nos. 5,194,639, 5,174,927 and 5,188,769 and WO 9,206,171, 9,206,151, 9,206,150 and 9,205,764 relate to various polyhydroxy fatty acid amide surfactants and uses thereof.

SUMMARY OF THE INVENTION

The present invention relates to novel gemini polyhydroxy fatty acid amide compounds having the formula:

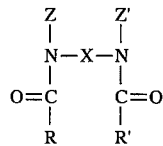

wherein: X is a bridging group having from about 2 to about 200 atoms; Z and Z' are the same or different alcohol-containing moieties having two or more hydroxyl groups (e.g., glycerol, and units derived from reducing sugars such as glucose, maltose and the like), or one of Z or Z' is hydrogen; and R and R' are the same or different hydrocarbyl moieties having from about 1 to about 21 carbon atoms and can be saturated, branched or unsaturated (e.g., oleoyl) and mixtures thereof.

The present invention also relates to compositions comprising:

(a) at least about 0.1% of a gemini polyhydroxy fatty acid amide compound as described hereinbefore; and (b) at least about 0.1% of one or more laundry or personal care composition materials.

The invention also provides a method for laundering fabrics or cleaning hard surfaces, comprising contacting said fabrics or hard surfaces with an aqueous solution containing at least about 10 ppm, preferably about 100 ppm–10,000 ppm, of a gemini polyhydroxy fatty acid amide compound, preferably with agitation.

All percentages, ratios and proportions herein are by weight, unless otherwise specified. All documents cited are incorporated herein by reference.

DETAILED DESCRIPTION OF THE INVENTION

1. Gemini Polyhydroxy Fatty Acid Amide Compounds

The present invention compounds are gemini polyhydroxy fatty acid amides having the formula:

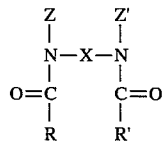

wherein: X is a bridging group having from about 2 to about 200 atoms; Z and Z' are the same or different alcohol-containing moieties having two or more hydroxyl groups (e.g., glycerol, and units derived from reducing sugars such as glucose, maltose and the like), or either one (but not both)

of Z or Z' is hydrogen; and R and R' are the same or different hydrocarbyl moieties having from about 1 to about 21 carbon atoms and can be saturated, branched or unsaturated (e.g., oleoyl) and mixtures thereof.

Preferred X are selected from the group consisting of substituted or unsubstituted, branched or linear alkyl, ether alkyl, amino alkyl, or amido alkyl moieties having from about 2 to about 15 carbon atoms. Preferred alkyl moieties are unsubstituted, linear alkyl moieties having the formula $-(CH_2)_n-$, wherein n is an integer from 2 to about 15, preferably from 2 to about 10, and most preferably from 2 to about 6; and also unsubstituted, branched alkyl moieties having from 3 to about 15 carbon atoms, preferably from 3 to about 10 carbon atoms, and most preferably from 3 to about 6 carbon atoms. Most preferred are ethylene and propylene (branched or linear) alkyl moieties. Also preferred are unsubstituted, branched or linear ether alkyl moieties having the formula $-R^2-(O-R^2)_m-$, wherein each $R^2$ is independently selected from $C_2-C_8$ branched or linear alkyl and/or aryl moieties (preferably ethyl, propyl or combinations thereof) and m is an integer from 1 to about 5. X may also be unsubstituted, branched or linear amino and/or amido alkyl moieties having the formula $-R^2-(N(R^3)-R^2)_m-$, wherein each $R^2$ is independently selected from $C_2-C_8$ branched or linear alkyl and/or aryl moieties (preferably ethyl, propyl or combinations thereof), m is an integer from 1 to about 5, and $R^3$ is selected from hydrogen, $C_1-C_5$ alkyl, and $-C(O)R^4-$, wherein $R^4$ is $C_1-C_{21}$ alkyl, including $-C(O)R$. The X moiety may be derived from commercially available amine compounds such as, for example, Jeffamines® (supplied by Texaco) such as JED600, JEDR148, JEDR192, JED230, JED2000, J-D230 and J-D400.

Preferred X moieties therefore include: $-(CH_2)_2-$, $-(CH_2)_3-$, $-(CH_2)_4-$, $-(CH_2)_5-$, $-(CH_2)_6-$, $-CH_2CH(CH_3)(CH_2)_3-$, $-(CH_2)_2-O-(CH_2)_2-$, $-(CH_2)_3-O-(CH_2)_3-$, $-(CH_2)_2-O-(CH_2)_3-$, $-(CH_2)_2-O-(CH_2)_2-O-(CH_2)_2-$, $-(CH_2)_3-O-(CH_2)_2-O-(CH_2)_3-$, $-(CH_2)_2-O-(CH_2)_3-O-(CH_2)_2-$, $-(CH_2)_2-NH-(CH_2)_2-$, $-(CH_2)_3-NH-(CH_2)_3-$, $-(CH_2)_2-NH-(CH_2)_3-$, $-(CH_2)_2-N(C(O)R)-(CH_2)_2-$, $-(CH_2)_3-N(C(O)R)-(CH_2)_3-$, $-(CH_2)_2-N(C(O)R)-(CH_2)_3-$, $-(CH_2)_2-NH(C_6H_4)NH-(CH_2)_2-$, $-(CH_2)_3-NH(C_6H_4)NH-(CH_2)_3-$, $-(CH_2)_2-NHCH_2(C_6H_4)CH_2NH-(CH_2)_2-$, $-(CH_2)_3-NHCH_2(C_6H_4)CH_2NH-(CH_2)_3-$, etc.

Preferred Z and Z' are independently selected from the group consisting of polyhydroxyhydrocarbyl moiety having a linear hydrocarbyl chain with at least 2 hydroxyl (in the case of glycerol) or at least 3 hydroxyls (in the case of other sugars) directly connected to the chain, or an alkoxylated derivative (preferably ethoxylated or propoxylated) thereof. Z and Z' preferably will be derived from a reducing sugar, more preferably Z and/or Z' is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for Z and Z'. It should be understood that it is by no means intended to exclude other suitable raw materials. Z and/or Z' preferably will be selected from the group consisting of $-CH_2-(CHOH)_p-CH_2OH$, $-CH(CH_2OH)-(CHOH)_{p-1}-CH_2OH$, $-CH_2-(CHOH)_2(CHOR^1)(CHOH)-CH_2OH$, where p is an integer from 1 to 5, inclusive, and $R^1$ is H or a cyclic mono- or polysaccharide, and alkoxylated derivatives thereof. Most preferred are glycityls wherein p is 4, particularly $-CH_2-(CHOH)_4-CH_2OH$.

Preferred R and R' are independently selected from the group consisting of $C_3-C_{21}$ hydrocarbyl moiety, preferably straight or branched chain $C_3-C_{13}$ alkyl or alkenyl, more preferably straight chain $C_5-C_{11}$ alkyl or alkenyl, most preferably straight chain $C_5-C_9$ alkyl or alkenyl, or mixtures thereof. R—CO—N< and/or R'—CO—N< can be, for example, cocamide, stearamide, oleamide, lauramide, myristamide, capricamide, palmitamide, tallowamide, etc.

Examples of compounds according to the present invention therefore include, but are not limited to:

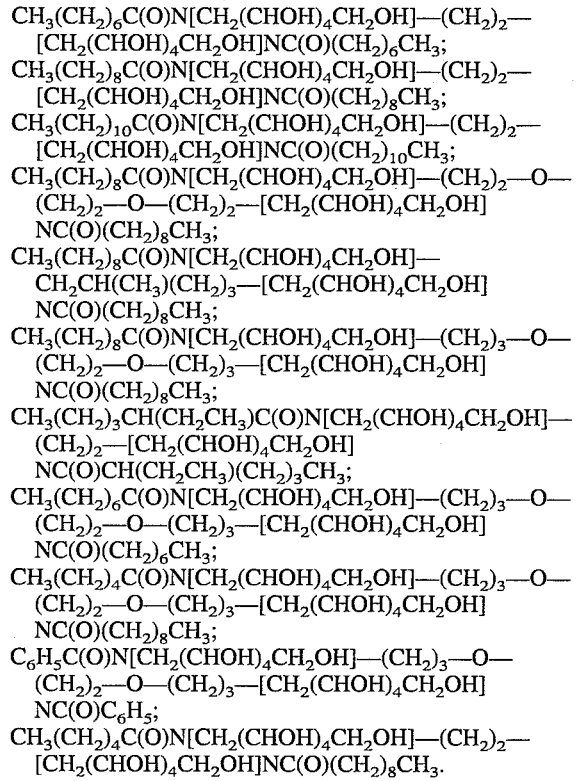

$CH_3(CH_2)_6C(O)N[CH_2(CHOH)_4CH_2OH]-(CH_2)_2-[CH_2(CHOH)_4CH_2OH]NC(O)(CH_2)_6CH_3$;
$CH_3(CH_2)_8C(O)N[CH_2(CHOH)_4CH_2OH]-(CH_2)_2-[CH_2(CHOH)_4CH_2OH]NC(O)(CH_2)_8CH_3$;
$CH_3(CH_2)_{10}C(O)N[CH_2(CHOH)_4CH_2OH]-(CH_2)_2-[CH_2(CHOH)_4CH_2OH]NC(O)(CH_2)_{10}CH_3$;
$CH_3(CH_2)_8C(O)N[CH_2(CHOH)_4CH_2OH]-(CH_2)_2-O-(CH_2)_2-O-(CH_2)_2-[CH_2(CHOH)_4CH_2OH]NC(O)(CH_2)_8CH_3$;
$CH_3(CH_2)_8C(O)N[CH_2(CHOH)_4CH_2OH]-CH_2CH(CH_3)(CH_2)_3-[CH_2(CHOH)_4CH_2OH]NC(O)(CH_2)_8CH_3$;
$CH_3(CH_2)_8C(O)N[CH_2(CHOH)_4CH_2OH]-(CH_2)_3-O-(CH_2)_2-O-(CH_2)_3-[CH_2(CHOH)_4CH_2OH]NC(O)(CH_2)_8CH_3$;
$CH_3(CH_2)_3CH(CH_2CH_3)C(O)N[CH_2(CHOH)_4CH_2OH]-(CH_2)_2-[CH_2(CHOH)_4CH_2OH]NC(O)CH(CH_2CH_3)(CH_2)_3CH_3$;
$CH_3(CH_2)_6C(O)N[CH_2(CHOH)_4CH_2OH]-(CH_2)_3-O-(CH_2)_2-O-(CH_2)_3-[CH_2(CHOH)_4CH_2OH]NC(O)(CH_2)_6CH_3$;
$CH_3(CH_2)_4C(O)N[CH_2(CHOH)_4CH_2OH]-(CH_2)_3-O-(CH_2)_2-O-(CH_2)_3-[CH_2(CHOH)_4CH_2OH]NC(O)(CH_2)_8CH_3$;
$C_6H_5C(O)N[CH_2(CHOH)_4CH_2OH]-(CH_2)_3-O-(CH_2)_2-O-(CH_2)_3-[CH_2(CHOH)_4CH_2OH]NC(O)C_6H_5$;
$CH_3(CH_2)_4C(O)N[CH_2(CHOH)_4CH_2OH]-(CH_2)_2-[CH_2(CHOH)_4CH_2OH]NC(O)(CH_2)_8CH_3$.

These compounds can be readily synthesized from the following disugar diamines:

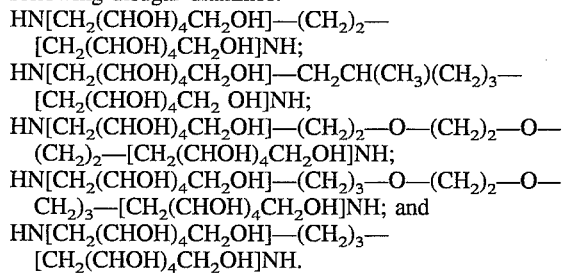

$HN[CH_2(CHOH)_4CH_2OH]-(CH_2)_2-[CH_2(CHOH)_4CH_2OH]NH$;
$HN[CH_2(CHOH)_4CH_2OH]-CH_2CH(CH_3)(CH_2)_3-[CH_2(CHOH)_4CH_2OH]NH$;
$HN[CH_2(CHOH)_4CH_2OH]-(CH_2)_2-O-(CH_2)_2-O-(CH_2)_2-[CH_2(CHOH)_4CH_2OH]NH$;
$HN[CH_2(CHOH)_4CH_2OH]-(CH_2)_3-O-(CH_2)_2-O-CH_2)_3-[CH_2(CHOH)_4CH_2OH]NH$; and
$HN[CH_2(CHOH)_4CH_2OH]-(CH_2)_3-[CH_2(CHOH)_4CH_2OH]NH$.

2. Compositions

In addition to comprising at least about 0.1% of a gemini polyhydroxy fatty acid amide compound as described hereinbefore, the present invention compositions further comprise at least about 0.1% of one or more laundry or personal care composition materials. Such materials useful in laundry or personal care products compositions include the following.

(a) Enzymes—Enzymes can be included in the formulations herein for a wide variety of fabric laundering purposes, including removal of protein-based, carbohydrate-based, or triglyceride-based stains, for example, and for the prevention of refugee dye transfer, and for fabric restoration. The enzymes to be incorporated include proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders and so on. In this respect bacterial or fungal enzymes are preferred, such as bacterial amylases and proteases, and fungal cellulases.

Enzymes are normally incorporated at levels sufficient to provide up to about 5 mg by weight, more typically about 0.01 mg to about 3 mg, of active enzyme per gram of the composition. Stated otherwise, the compositions herein will typically comprise from about 0.001% to about 5%, preferably 0.01%–1% by weight of a commercial enzyme preparation. Protease enzymes are usually present in such commercial preparations at levels sufficient to provide from 0.005 to 0.1 Anson units (AU) of activity per gram of composition.

Suitable examples of proteases are the subtilisins which are obtained from particular strains of B.subtilis and B.licheniforms. Another suitable protease is obtained from a strain of Bacillus, having maximum activity throughout the pH range of 8–12, developed and sold by Novo Industries A/S under the registered trade name ESPERASE. The preparation of this enzyme and analogous enzymes is described in British Patent Specification No. 1,243,784 of Novo. Proteolytic enzymes suitable for removing protein-based stains that are commercially available include those sold under the tradenames ALCALASE and SAVINASE by Novo Industries A/S (Denmark) and MAXATASE by International Bio-Synthetics, Inc. (The Netherlands). Other proteases include Protease A (see European Patent Application 130,756, published Jan. 9, 1985) and Protease B (see European Patent Application Serial No. 87303761.8, filed Apr. 28, 1987, and European Patent Application 130,756, Bott et al, published Jan. 9, 1985).

Amylases include, for example, α-amylases described in British Patent Specification No. 1,296,839 (Novo), RAPIDASE, International Bio-Synthetics, Inc. and TERMAMYL, Novo Industries.

The cellulase usable in the present invention include both bacterial or fungal cellulase. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from *Humicola insolens* and Humicola strain DSM1800 or a cellulase 212-producing fungus belonging to the genus Aeromonas, and cellulase extracted from the hepatopancreas of a marine mollusk (Dolabella Auricula Solander). Suitable cellulases are also disclosed in GB-A-2.075.028; GB-A-2.095.275 and DE-OS-2.247.832.

Suitable lipase enzymes for detergent usage include those produced by microorganisms of the Pseudomonas group, such as *Pseudomonas stutzeri* ATCC 19.154, as disclosed in British Patent 1,372,034. See also lipases in Japanese Patent Application 53,20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex *Chromobacter viscosum*, e.g. *Chromobacter viscosum* var. lipolyticum NRRLB 3673, commercially available from Toyo Jozo Co., Tagata, Japan; and further Chromobacter viscosum lipases from U.S. Biochemical Corp., U.S.A. and Disoynth Co., The Netherlands, and lipases ex *Pseudomonas gladioli*. The LIPOLASE enzyme derived from *Humicola lanuginosa* and commercially available from Novo (see also EPO 341,947) is a preferred lipase for use herein.

Peroxidase enzymes are used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985, both. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

(b) Enzyme Stabilizers—The enzymes employed herein are stabilized by the presence of water-soluble sources of calcium and/or magnesium ions in the finished compositions which provide such ions to the enzymes. (Calcium ions are generally somewhat more effective than magnesium ions and are preferred herein if only one type of cation is being used.) Additional stability can be provided by the presence of various other art-disclosed stabilizers, especially borate species: see Severson, U.S. Pat. No. 4,537,706. Typical detergents, especially liquids, will comprise from about 1 to about 30, preferably from about 2 to about 20, more preferably from about 5 to about 15, and most preferably from about 8 to about 12, millimoles of calcium ion per liter of finished composition. This can vary somewhat, depending on the amount of enzyme present and its response to the calcium or magnesium ions. The level of calcium or magnesium ions should be selected so that there is always some minimum level available for the enzyme, after allowing for complexation with builders, fatty acids, etc., in the composition. Any water-soluble calcium or magnesium salt can be used as the source of calcium or magnesium ions, including, but not limited to, calcium chloride, calcium sulfate, calcium malate, calcium maleate, calcium hydroxide, calcium formate, and calcium acetate, and the corresponding magnesium salts. A small amount of calcium ion, generally from about 0.05 to about 0.4 millimoles per liter, is often also present in the composition due to calcium in the enzyme slurry and formula water. In solid detergent compositions the formulation may include a sufficient quantity of a water-soluble calcium ion source to provide such amounts in the laundry liquor. In the alternative, natural water hardness may suffice.

It is to be understood that the foregoing levels of calcium and/or magnesium ions are sufficient to provide enzyme stability. More calcium and/or magnesium ions can be added to the compositions to provide an additional measure of grease removal performance. Accordingly, as a general proposition the compositions herein will typically comprise from about 0.05% to about 2% by weight of a water-soluble source of calcium or magnesium ions, or both. The amount can vary, of course, with the amount and type of enzyme employed in the composition.

The compositions herein may also optionally, but preferably, contain various additional stabilizers, especially borate-type stabilizers. Typically, such stabilizers will be used at levels in the compositions from about 0.25% to about 10%, preferably from about 0.5% to about 5%, more preferably from about 0.75% to about 3%, by weight of boric acid or other borate compound capable of forming boric acid in the composition (calculated on the basis of boric acid). Boric acid is preferred, although other compounds such as boric oxide, borax and other alkali metal borates (e.g., sodium ortho-, meta- and pyroborate, and sodium pentaborate) are suitable. Substituted boric acids (e.g., phenylboronic acid, butane boronic acid, and p-bromo phenylboronic acid) can also be used in place of boric acid.

(c) Bleaching Compounds—Bleaching Agents and Bleach Activators—The detergent compositions herein may optionally contain bleaching agents or bleaching compositions containing a bleaching agent and one or more bleach activators. When present, bleaching agents will typically be at levels of from about 1% to about 30%, more typically from about 5% to about 20%, of the detergent composition, especially for fabric laundering. If present, the amount of bleach activators will typically be from about 0.1% to about 60%, more typically from about 0.5% to about 40% of the bleaching composition comprising the bleaching agent-plus-bleach activator.

The bleaching agents used herein can be any of the bleaching agents useful for detergent compositions in textile cleaning, hard surface cleaning, or other cleaning purposes that are now known or become known. These include oxygen bleaches as well as other bleaching agents. Perborate bleaches, e.g., sodium perborate (e.g., mono- or tetra-hydrate) can be used herein.

Another category of bleaching agent that can be used without restriction encompasses percarboxylic acid bleaching agents and salts thereof. Suitable examples of this class of agents include magnesium monoperoxyphthalate hexahydrate, the magnesium salt of metachloro perbenzoic acid, 4-nonylamino-4-oxoperoxybutyric acid and diperoxydodecanedioic acid. Such bleaching agents are disclosed in U.S. Pat. No. 4,483,781, Hartman, issued Nov. 20, 1984, U.S. patent application Ser. No. 740,446, Burns et al, filed Jun. 3, 1985, European Patent Application 0,133,354, Banks et al, published Feb. 20, 1985, and U.S. Pat. No. 4,412,934, Chung et al, issued Nov. 1, 1983. Highly preferred bleaching agents also include 6-nonylamino-6-oxoperoxycaproic acid as described in U.S. Pat. No. 4,634,551, issued Jan. 6, 1987 to Burns et al.

Peroxygen bleaching agents can also be used. Suitable peroxygen bleaching compounds include sodium carbonate peroxyhydrate and equivalent "percarbonate" bleaches, sodium pyrophosphate peroxyhydrate, urea peroxyhydrate, and sodium peroxide. Persulfate bleach (e.g., OXONE, manufactured commercially by DuPont) can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

Mixtures of bleaching agents can also be used.

Peroxygen bleaching agents, the perborates, the percarbonates, etc., are preferably combined with bleach activators, which lead to the in situ production in aqueous solution (i.e., during the washing process) of the peroxy acid corresponding to the bleach activator. Various nonlimiting examples of activators are disclosed in U.S. Pat. No. 4,915,854, issued Apr. 10, 1990 to Mao et al, and U.S. Pat. No. 4,412,934. The nonanoyloxybenzene sulfonate (NOBS) and tetraacetyl ethylene diamine (TAED) activators are typical, and mixtures thereof can also be used. See also U.S. Pat. No. 4,634,551 for other typical bleaches and activators useful herein.

Highly preferred amido-derived bleach activators are those of the formulae:

$R^1N(R^5)C(O)R^2C(O)L$ or $R^1C(O)N(R^5)R^2C(O)L$ wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. A leaving group is any group that is displaced from the bleach activator as a consequence of the nucleophilic attack on the bleach activator by the perhydrolysis anion. A preferred leaving group is phenyl sulfonate.

Preferred examples of bleach activators of the above formulae include (6-octanamido-caproyl)oxybenzenesulfonate, (6-nonanamidocaproyl)oxybenzenesulfonate, (6-decanamido-caproyl)oxybenzenesulfonate, and mixtures thereof as described in U.S. Pat. No. 4,634,551.

Another class of bleach activators comprises the benzoxazin-type activators disclosed by Hodge et al in U.S. Pat. No. 4,966,723, issued Oct. 30, 1990. A highly preferred activator of the benzoxazin-type is:

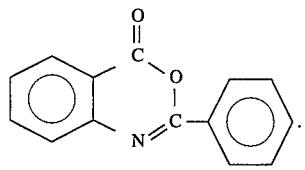

Still another class of preferred bleach activators includes the acyl lactam activators, especially acyl caprolactams and acyl valerolactams of the formulae:

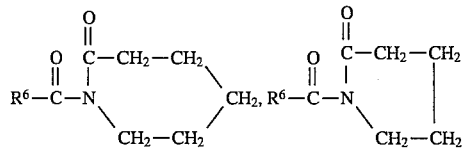

wherein $R^6$ is H or an alkyl, aryl, alkoxyaryl, or alkaryl group containing from 1 to about 12 carbon atoms. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof. See also U.S. Pat. No. 4,545,784, issued to Sanderson, Oct. 8, 1985, which discloses acyl caprolactams, including benzoyl caprolactam, adsorbed into sodium perborate.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. See U.S. Pat. No. 4,033,718, issued Jul. 5, 1977 to Holcombe et al. If used, detergent compositions will typically contain from about 0.025% to about 1.25%, by weight, of such bleaches, especially sulfonate zinc phthalocyanine.

(d) Builders—Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2SiO_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

$$Mz(zAlO_2)_y] \cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

$$Na_{12}[(AlO_2)_{12}(SiO_2)_{12}] \cdot xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with aeolite and/or layered silicate builders. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy- 1,1-diphosphonate and other known phosphonates (see, for example, U.S. Pat. Nos. 3,159,581; 3,213,030; 3,422,021; 3,400,148 and 3,422,137) can also be used.

(e) Polymeric Soil Release Agent—Any polymeric soil release agent known to those skilled in the art can optionally be employed in the compositions and processes of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

The polymeric soil release agents useful herein especially include those soil release agents having: (a) one or more nonionic hydrophile components consisting essentially of (i) polyoxyethylene segments with a degree of polymerization of at least 2, or (ii) oxypropylene or polyoxypropylene segments with a degree of polymerization of from 2 to 10, wherein said hydrophile segment does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate:$C_3$ oxyalkylene terephthalate units is about 2:1 or lower, (ii) $C_4$–$C_6$ alkylene or oxy $C_4$–$C_6$ alkylene segments, or mixtures therein, (iii) poly (vinyl ester) segments, preferably poly9vinyl acetate), having a degree of polymerization of at least 2, or (iv) $C_1$–$C_4$ alkyl ether or $C_4$ hydroxyalkyl ether xubstituents, or mixtures therein, wherein said substituents are present in the form of $C_1$–$C_4$ alkyl ether or $C_4$ hydroxyalkyl ether cellulose derivatives, or mixtures therein, and such cellulose derivatives are amphiphilic, whereby they have a sufficient level of $C_1$–$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a)(i) will have a degree of polymerization of from about 200, although higher levels can be used, preferably from 3 to about 150, more preferably from 6 to about 100. Suitable oxy $C_4$–$C_6$ alkylene hydrophobe segments include, but are not limited to, end-caps of polymeric soil release agents such as $MO_3S(CH_2)_nOCH_2CH_2O$—, where M is sodium and n is an integer from 4–6, as disclosed in U.S. Pat. No. 4,721,580, issued Jan. 26, 1988 to Gosselink.

Polymeric soil release agents useful in the present invention also include cellulosic derivatives such as hydroxyether cellulosic polymers, copolymeric blocks of ethylene terephthalate or propylene terephthalate with polyethylene oxide or polypropylene oxide terephthalate, and the like. Such agents are commercially available and include hydroxyethers of cellulose such as METHOCEL (Dow). Cellulosic soil release agents for use herein also include those selected from the group consisting of $C_1$–$C_4$ alkyl and $C_4$ hydroxyalkyl cellulose; see U.S. Pat. No. 4,000,093, issued Dec. 28, 1976 to Nicol, et al.

Soil release agents characterized by poly(vinyl ester) hydrophobe segments include graft copolymers of poly(vinyl ester), e.g., $C_1$–$C_6$ vinyl esters, preferably poly(vinyl acetate) grafted onto polyalkylene oxide backbones, such as polyethylene oxide backbones. See European Patent Application 0 219 048, published Apr. 22, 1987 by Kud, et al. Commercially available soil release agents of this kind include the SOKALAN type of material, e.g., SOKALAN HP-22, available from BASF (West Germany).

One type of preferred soil release agent is a copolymer having random blocks of ethylene terephthalate and polyethylene oxide (PEO) terephthalate. The molecular weight of this polymeric soil release agent is in the range of from about 25,000 to about 55,000. See U.S. Pat. No. 3,959,230 to Hays, issued May 25, 1976 and U.S. Pat. No. 3,893,929 to Basadur issued Jul. 8, 1975.

Another preferred polymeric soil release agent is a polyester with repeat units of ethylene terephthalate units containins 10–15% by weight of ethylene terephthalate units together with 90–80% by weight of polyoxyethylene terephthalate units, derived from a polyoxyethylene glycol of average molecular weight 300–5,000. Examples of this polymer include the commercially available material ZELCON 5126 (from Dupont) and MILEASE T (from ICI). See also U.S. Pat. No. 4,702,857, issued Oct. 27, 1987 to Gosselink.

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451, issued Nov. 6, 1990 to J. J. Scheibel and E. P. Gosselink. Other suitable polymeric soil release agents include the terephthalate polyesters of U.S. Pat. No. 4,711,730, issued Dec. 8, 1987 to Gosselink et al, the anionic end-capped oligomeric esters of U.S. Pat. No. 4,721,580, issued Jan. 26, 1988 to Gosselink, and the block polyester oligomeric compounds of U.S. Pat. No. 4,702,857, issued Oct. 27, 1987 to Gosselink.

Preferred polymeric soil release agents also include the soil release agents of U.S. Pat. No. 4,877,896, issued Oct. 31, 1989 to Maldonado et al, which discloses anionic, especially sulfoarolyl, end-capped terephthalate esters.

If utilized, soil release agents will generally comprise from about 0.01% to about 10.0%, by weight, of the detergent compositions herein, typically from about 0.1% to about 5%, preferably from about 0.2% to about 3.0%.

(f) Chelating Agents—The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions.

(g) Clay Soil Removal/Anti-redeposition Agents—The compositions of the present invention can also optionally contain water-soluble ethoxylated amines having clay soil removal and antiredeposition properties. Granular detergent compositions which contain these compounds typically contain from about 0.01% to about 10.0% by weight of the water-soluble ethoxylates amines; liquid detergent compositions typically contain about 0.01% to about 5%.

The most preferred soil release and anti-redeposition agent is ethoxylated tetraethylenepentamine. Exemplary ethoxylated amines are further described in U.S. Pat. No. 4,597,898, VanderMeer, issued Jul. 1, 1986. Another group of preferred clay soil removal-antiredeposition agents are the cationic compounds disclosed in European Patent Application 111,965, Oh and Gosselink, published Jun. 27, 1984. Other clay soil removal/antiredeposition agents which can be used include the ethoxylated amine polymers disclosed in European Patent Application 111,984, Gosslink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985. Other clay soil removal and/or anti redeposition agents known in the art can also be utilized in the compositions herein. Another type of preferred antiredeposition agent includes the carboxy methyl cellulose (CMC) materials. These materials are well known in the art.

(h) Polymeric Dispersing Agents—Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crustal growth inhibition, particulate soil release peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein or monomeric segments, containing no carboxylate radicals such as finylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in Diehl, U.S. Pat. No. 3,308,067, issued Mar. 7, 1967.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982.

Another polymeric material which can be included is polyethylene glycol (PEG). PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used, especially in conjunction with zeolite builders. Dispersing agents such as polyaspartate preferably have a molecular weight (avg.) of about 10,000.

(i) Brightener—Any optical brighteners or other brightening or whitening agents known in the art can be incorporated at levels typically from about 0.05% to about 1.2%, by weight, into the detergent compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982).

Specific examples of optical brighteners which are useful in the present compositions are those identified in U.S. Pat. No. 4,790,856, issued to Wixon on Dec. 13, 1988. These brighteners include the PHORWHITE series of brighteners from Verona. Other brighteners disclosed in this reference include: Tinopal UNPA, Tinopal CBS and Tinopal 5BM; available from Ciba-Geigy; Artic White CC and Artic White CWD, available from Hilton-Davis, located in Italy; the 2-(4-stryl-phenyl)-2H-napthol[1,2-d]triazoles; 4,4'-bis-(1,2,3-triazol-2-yl)-stil-benes; 4,4'-bis(stryl)bisphenyls; and the aminocoumarins. Specific examples of these brighteners include 4-methyl-7-diethyl-amino coumarin; 1,2-bis(-venzimidazol-2-yl(ethylene; 1,3-diphenyl-phrazolines; 2,5-bis-(benzoxazol-2-yl)thiophene; 2-stryl-napth-[1,2-d]oxazole; and 2-(stilbene-4-yl)-2H-naphtho-[1,2-d]triazole. See also U.S. Pat. No. 3,646,015, issued Feb. 29, 1972 to Hamilton. Anionic brighteners are preferred herein.

(j) Suds Suppressors—Compounds for reducing or suppressing the formation of suds can be incorporated into the compositions of the present invention. Suds suppression can be of particular A wide variety of materials may be used as suds suppressors, and suds suppressors are well known to those skilled in the art. See, for example, Kirk Othmer Encyclopedia of Chemical Technology, Third Edition, Volume 7, pages 430–447 (John Wiley & Sons, Inc., 1979). One category of suds suppressor of particular interest encompasses monocarboxylic fatty acids and soluble salts therein. See U.S. Pat. No. 2,954,347, issued Sep. 27, 1960 to Wayne St. John. The monocarboxylic fatty acids and salts thereof used as suds suppressor typically have hydrocarbyl chains of 10 to about 24 carbon atoms, preferably 12 to 18 carbon atoms. Suitable salts include the alkali metal salts such as sodium, potassium, and lithium salts, and ammonium and alkanolammonium salts.

The detergent compositions herein may also contain non-surfactant suds suppressors. These include, for example: high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), etc. Other suds inhibitors include N-alkylated amino triazines such as tri- to hexa-alkylmelamines or di- to tetra-alkyldiamine chlortriazines formed as products of cyanuric chloride with two or three moles of a primary or secondary amine containing 1 to 24 carbon atoms, propylene oxide, and monostearyl phosphates such as monostearyl alcohol phosphate ester and monostearyl di-alkali metal (e.g., K, Na, and Li) phosphates and phosphate esters. The hydrocarbons such as paraffin and haloparaffin can be utilized in liquid form. The liquid hydrocarbons will be liquid at room temperature and atmospheric pressure, and will have a pour point in the range of about −40° C. and about 50° C., and a minimum boiling point not less than about 110° C. (atmospheric pressure). It is also known to utilize waxy hydrocarbons, preferably having a melting point below about 100° C. The hydrocarbons constitute a preferred category of suds suppressor for detergent compositions. Hydrocarbon suds suppressors are described, for example, in U.S. Pat. No. 4,265,779, issued May 5, 1981 to Gandolfo et al. The hydrocarbons, thus, include aliphatic, alicyclic, aromatic, and heterocyclic saturated or unsaturated hydrocarbons having from about 12 to about 70 carbon atoms. The term "paraffin," as used in this suds suppressor discussion, is intended to include mixtures of true paraffins and cyclic hydrocarbons.

Another preferred category of non-surfactant suds suppressors comprises silicone suds suppressors. This category includes the use of polyorganosiloxane oils, such as polydimethylsiloxane, dispersions or emulsions of polyorganosiloxane oils or resins, and combinations of polyorganosiloxane with silica particles wherein the polyorganosiloxane is chemisorbed or fused onto the silica. Silicone suds suppressors are well known in the art and are, for example, disclosed in U.S. Pat. No. 4,265,779, issued May 5, 1981 to Gandolfo et al and European Patent Application No. 89307851.9, published Feb. 7, 1990, by Starch, M. S.

Other silicone suds suppressors are disclosed in U.S. Pat. No. 3,455,839 which relates to compositions and processes for defoaming aqueous solutions by incorporating therein small amounts of polydimethylsiloxane fluids.

Mixtures of silicone and silanated silica are described, for instance, in German Patent Application DOS 2,124,526. Silicone defoamers and suds controlling agents in granular detergent compositions are disclosed in U.S. Pat. No. 3,933,672, Bartolotta et al, and in U.S. Pat. No. 4,652,392, Baginski et al, issued Mar. 24, 1987.

An exemplary silicone based suds suppressor for use herein is a suds suppressing amount of a suds controlling agent consisting essentially of:

(i) polydimethylsiloxane fluid having a viscosity of from about 20 cs. to about 1,500 cs. at 25° C.;

(ii) from about 5 to about 50 parts per 100 parts by weight of (i) of siloxane resin composed of $(CH_3)_3SiO_{1/2}$ units of $SiO_2$ units in a ratio of from $(CH_3)_3SiO_{1/2}$ units and to $SiO_2$ units of from about 0.6:1 to about 1.2:1; and (iii) from about 1 to about 20 parts per 100 parts by weight of (i) of a solid silica gel.

In the preferred silicone suds suppressor used herein, the solvent for a continuous phase is made up of certain polyethylene glycols or polyethylene-polypropylene glycol copolymers or mixtures thereof (preferred), and not polypropylene glycol. The primary silicone suds suppressor is branched/crosslinked and not linear.

To illustrate this point further, typical liquid laundry detergent compositions with controlled suds will optionally comprise from about 0.001 to about 1, preferably from about 0.01 to about 0.7, most preferably from about 0.05 to about 0.5, weight % of said silicone suds suppressor, which comprises (1) a nonaqueous emulsion of a primary antifoam agent which is a mixture of (a) a polyorganosiloxane, (b) a resinous siloxane or a silicone resin-producing silicone compound, (c) a finely divided filler material, and (d) a catalyst to promote the reaction of mixture components (a), (b) and (c), to form silanolates; (2) at least one nonionic silicone surfactant; and (3) polyethylene glycol or a copolymer of polyethylene-polypropylene glycol having a solubility in water at room temperature of more than about 2 weight %; and without polypropylene glycol. Similar amounts can be used in granular compositions, gels, etc. See also U.S. Pat. Nos. 4,978,471, Starch, issued Dec. 18, 1990, and 4,983,316, Starch, issued Jan. 8, 1991, and U.S. Pat. Nos. 4,639,489 and 4,749,740, Aizawa et al at column 1, line 46 through column 4, line 35.

The silicone suds suppressor herein preferably comprises polyethylene glycol and a copolymer of polyethylene glycol/polypropylene glycol, all having an average molecular weight of less than about 1,000, preferably between about 100 and 800. The polyethylene glycol and polyethylene/polypropylene copolymers herein have a solubility in water at room temperature of more than about 2 weight %, preferably more than about 5 weight %.

The preferred solvent herein is polyethylene glycol having an average molecular weight of less than about 1,000, more preferably between about 100 and 800, most preferably between 200 and 400, and a copolymer of polyethylene glycol/polypropylene glycol, preferably PPG 200/PEG 300. Preferred is a weight ratio of between about 1:1 and 1:10, most preferably between 1:3 and 1:6, of polyethylene glycol:copolymer of polyethylene-polypropylene glycol.

The preferred silicone suds suppressors used herein do not contain polypropylene glycol, particularly of 4,000 molecular weight. They also preferably do not contain block copolymers of ethylene oxide and propylene oxide, like PLURONIC L101.

Other suds suppressors useful herein comprise the secondary alcohols (e.g., 2-alkyl alkanols) and mixtures of such alcohols with silicone oils, such as the silicones disclosed in U.S. Pat. Nos. 4,798,679, 4,075,118 and EP 150,872. The secondary alcohols include the $C_6$–$C_{16}$ alkyl alcohols having a $C_1$–$C_{16}$ chain. A preferred alcohol is 2-butyl octanol, which is available from Condea under the trademark ISOFOL 12. Mixtures of secondary alcohols are available under the trademark ISALCHEM 123 from Enichem. Mixed suds suppressors typically comprise mixtures of alcohol+silicone at a weight ratio of 1:5 to 5:1.

For any detergent compositions to be used in automatic laundry washing machines, suds should not form to the extent that they overflow the washing machine. Suds suppressors, when utilized, are preferably present in a "suds suppressing amount. By "suds suppressing amount" is meant that the formulator of the composition can select an amount of this suds controlling agent that will sufficiently control the suds to result in a low-sudsing laundry detergent for use in automatic laundry washing machines.

The compositions herein will generally comprise from 0% to about 5% of suds suppressor. When utilized as suds suppressors, monocarboxylic fatty acids, and salts therein, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0%, by weight, of the detergent composition, although higher amounts may be used. This upper limit is practical in nature, due primarily to concern with keeping costs minimized and effectiveness of lower amounts for effectively controlling sudsing. Preferably from about 0.01% to about 1% of silicone suds suppressor is used, more preferably from about 0.25% to about 0.5%. As used herein, these weight percentage values include any silica that may be utilized in combination with polyorganosiloxane, as well as any adjunct materials that may be utilized. Monostearyl phosphate suds suppressors are generally utilized in amounts ranging from about 0.1% to about 2%, by weight, of the composition. Hydrocarbon suds suppressors are typically utilized in amounts ranging from about 0.01% to about 5.0%, although higher levels can be used. The alcohol suds suppressors are typically used at 0.2%–3% by weight of the finished compositions.

(k) Fabric Softeners—Various through-the-wash fabric softeners, especially the impalpable smectite clays of U.S. Pat. No. 4,062,647, Storm and Nirschl, issued Dec. 13, 1977, as well as other softener clays known in the art, can optionally be used typically at levels of from about 0.5% to about 10% by weight in the present compositions to provide fabric softener benefits concurrently with fabric cleaning. Clay softeners can be used in combination with amine and cationic softeners as disclosed, for example, in U.S. Pat. No. 4,375,416, Crisp et al, Mar. 1, 1983 and U.S. Pat. No. 4,291,071, Harris et al, issued Sep. 22, 1981.

(l) Detersive Surfactants—Nonlimiting examples of surfactants useful herein typically at levels from about 1% to about 55%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)$ $CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10}$–$C_{18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are listed in standard texts.

The present invention compositions may also comprise oleoyl sarcosinate, in its acid and/or salt form selected as desired for the compositions and uses herein, having the following formula:

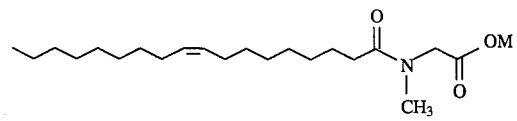

wherein M is hydrogen or a cationic moiety. Preferred M are hydrogen and alkali metal salts, especially sodium and potassium. Oleoyl sarcosinate is commercially available, for example as Hamposyl O supplied by W. R. Grace & Co. Compositions according to the present invention can typically comprise from about 0.1% to about 55%, preferably from about 1% to about 20%, and most preferably from about 3% to about 15%, of oleoyl sarcosinate by weight of the composition.

In addition to the commercially-available oleoyl sarcosinate, oleoyl sarcosinate useful herein can also preferably be prepared from the ester (preferably the methyl ester) of oleic acid and a sarcosine salt (preferably the sodium salt) under anhydrous reaction conditions in the presence of a base catalyst with a basicity equal to or greater than alkoxide catalyst (preferably sodium methoxide). For example, the reaction may be illustrated by the scheme:

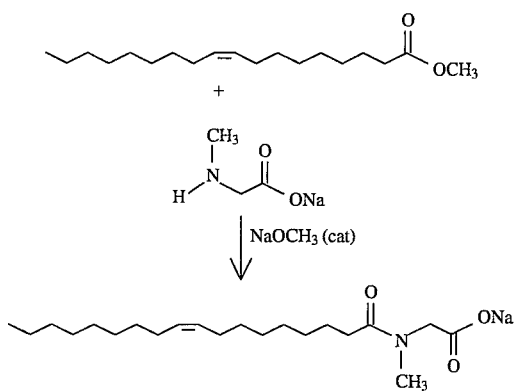

This salt may optionally be neutralized to form the oleoyl sarcosinate in its acid form.

The preferred method for preparing oleoyl sarcosinate is conducted at a temperature from about 80° C. to about 200° C., especially from about 120° C. to about 200° C. It is preferred to conduct the reaction without solvent although alcohol solvents which have a boiling point of at least 100° C. and are stable to the reaction conditions (ie. glycerol is not acceptable) can be used. The reaction may proceed in about 85% yield with a molar ratio of methyl ester reactant to sarcosine salt reactant to basic catalyst of about 1:1:0.05–0.2.

Methyl ester mixtures derived from high oleic content natural oils (preferably having at least about 60%, more preferably at least about 75%, and most preferably at least about 90% oleic content) are especially preferred as starting materials. Examples include high-oleic sunflower and rapeseed/canola oil. In addition, a high-oleic methyl ester fraction derived from either palm kernel oil or tallow is acceptable. It is to be understood that such oils typically will contain some levels of impurities, including some fatty acid impurities that may be converted to sarcosinate compounds by this synthesis method. For example, commodity canola/rapeseed oil may comprise a majority of oleic acid, and a mixture of fatty acid impurities such as palmitic, stearic, linoleic, linolenic and/or eicosenoic acid, some or all of which are converted to the sarcosinate by this reaction method. If desired for formulation purposes, some or all of such impurity materials may be excluded from the starting oil before preparing the oleoyl sarcosinate to be used in the present compositions.

Finally, sarcosine remaining in the reaction mixture can be converted to an amide by addition of maleic or acetic anhydride to the mixture, thereby minimizing the sarcosine content and any potential for formation of undesired nitrogen-containing impurities.

The synthesis of oleoyl sarcosinate may be carried out as follows to prepare the sodium oleoyl sarcosinate.

Synthesis of Oleoyl Amide of Sarcosine Sodium Salt—A 2 L, 3-neck, round bottom flask is fitted with thermometer, Dean-Stark trap with condenser, mechanical stirring, and a gas inlet adapter through which nitrogen is passed over the reaction mixture. The reaction vessel is charged with sarcosine (43.3 g, 0.476 mol), sodium methoxide 25% in methanol (97.7 g, 0.452 mol), and methanol (400 mL). The reaction is refluxed 15 min to neutralize the sarcosine and then methyl ester derived from Cargill regular high-oleyl sunflower oil (148.25 g, 0.5 mol) is added. After the methanol is removed with the Dean-Stark trap, reaction mixture is heated to 170° C. for 1 hr to drive off any water. The reaction is initiated by the addition of sodium methoxide 25% in methanol (15.4 g, 0.0714 mol). Reaction is kept at 170° C. for 2.5 hr during which methanol is collected in the Dean-Stark trap. The reaction is allowed to cool slightly and then methanol (200 g) is added. Maleic anhydride (9.43 g, 0.095 mol) is added to the methanol solution and the reaction is stirred at 60° C. for 0.5 hr. Then most of the methanol is removed by rotary evaporation and acetone (2 L) is added to precipitate the product. The product is collected by suction filtration and allowed to air dry to give an off-white solid. Analysis of the reaction mixture by GC indicates the majority of the product is oleoyl sarcosinate, with minor amounts of the following impurities: sarcosine, oleic acid, and the sarcosinates derived from palmitic acid, stearic acid, and linoleic acid.

(m) Dye Transfer Inhibiting Agents—The compositions of the present invention can also optionally include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrolidone and N-vinylimidazole, peroxidases, and mixtures thereof. If used, these agents typically comprise from about 0.01% to about 10% by weight of the composition, preferably from about 0.01% to about 5%, and more preferably from about 0.05% to about 2%.

More specifically, the polyamine N-oxide polymers preferred for use herein contain units having the following structural formula: R—$A_x$—P; wherein P is a polymerizable unit to which an N—O group can be attached or the N—O group can form part of the polymerizable unit or the N—O group can be attached to both units; A is one of the following structures: —NC(O)—, —C(O)O—, —S—, —O—, —N=; x is 0 or 1; and R is aliphatic, ethoxylated aliphatics, aromatics, heterocyclic or alicyclic groups or any combination thereof to which the nitrogen of the N—O group can be attached or the N—O group is part of these groups. Preferred polyamine N-oxides are those wherein R is a heterocyclic group such as pyridine, pyrrole, imidazole, pyrrolidine, piperidine and derivatives thereof.

The N—O group can be represented by the following general structures:

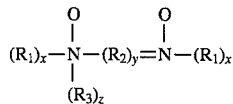

wherein $R_1$, $R_2$, $R_3$ are aliphatic, aromatic, heterocyclic or alicyclic groups or combinations thereof; x, y and z are 0 or 1; and the nitrogen of the N—O group can be attached or form part of any of the aforementioned groups. The amine oxide unit of the polyamine N-oxides has a pKa<10, preferably pKa<7, more preferred pKa<6.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof. These polymers include random or block copolymers where one monomer type is an amine N-oxide and the other monomer type is an N-oxide. The amine N-oxide polymers typically have a ratio of amine to the amine N-oxide of 10:1 to 1:1,000,000. However, the number of amine oxide groups present in the polyamine oxide polymer can be varied by appropriate copolymerization or by an appropriate degree of N-oxidation. The polyamine oxides can be obtained in almost any degree of polymerization. Typically, the average molecular weight is within the range of 500 to 1,000,000; more preferred 1,000 to 500,000; most preferred 5,000 to 100,000.

Copolymers of N-vinylpyrolidone and N-vinylimidazole polymers (referred to as "PVPI") are also preferred for use herein. Preferably the PVPI has an average molecular weight range from 5,000 to 1,000,000, more preferably from 5,000 to 200,000, and most preferably from 10,000 to 20,000. (The average molecular weight range is determined by light scattering as described in Barth, et al., *Chemical Analysis,* Vol 113. "Modern Methods of Polymer Characterization", the disclosures of which are incorporated herein by reference.) The PVPI copolymers typically have a molar ratio of N-vinylimidazole to N-vinylpyrrolidone from 1:1 to 0.2:1, more preferably from 0.8:1 to 0.3:1, most preferably from 0.6:1 to 0.4:1. These copolymers can be either linear or branched.

The present invention compositions may also contain a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field; see, for example, EP-A-262,897 and EP-A-256,696, incorporated herein by reference. Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50:1, and more preferably from about 3:1 to about 10:1.

(n) Other Ingredients—A wide variety of other ingredients useful in detergent compositions can be included in the compositions herein, including other active ingredients, carders, hydrotropes, processing aids, dyes or pigments, perfumes, solvents for liquid formulations, solid fillers for bar compositions, etc. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, 0.1%–2%, to provide additional suds and to enhance grease removal performance.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT D10, DeGussa) is admixed with a proteolytic enzyme solution containing 3%–5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Liquid detergent compositions can contain water and other solvents as carders. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers.

The detergent compositions herein will preferably be formulated such that, during use in aqueous cleaning operations, the wash water will have a pH of between about 6.5 and about 11, preferably between about 7.5 and 10.5. Liquid dishwashing product formulations preferably have a pH between about 6.8 and about 9.0. Laundry products are typically at pH 9–11. Techniques for controlling pH at recommended usage levels include the use of buffers, alkalis, acids, etc., and are well known to those skilled in the art.

By "interfacial tension" ("IFT") herein is meant the tension measured at the oil/water interface. IFT measurements using the spinning drop technique, are disclosed by Cayias, Schechter and Wade, "The Measurement of Low Interfacial Tension via the Spinning Drop Technique", ACS Symposium Series No. 8 (1975) ADSORPTION AT INTERFACES, beginning at page 234. Equipment for running IFT measurements is currently available from W. H. Wade, Depts. of Chemistry and Chemical Engineering, The University of Texas at Austin, Austin, Tex. 78712.

By "low interfacial tension" herein is meant an IFT which is sufficiently low that "spontaneous emulsification", i.e., rapid emulsification with little or no mechanical agitation, can occur. IFT's of about 0.15 dynes/cm, and below, even as low as 0.06 dynes/cm, can easily be secured by the present compositions at usage levels of 50–20,000 ppm.

The "spontaneous emulsification" of greasy/oily soils provided by the compositions herein can be simply, but convincingly, demonstrated by admixing a detergent composition in accordance with the invention with water. After dissolution of the detergent, a few drops of oil to which a colored oil-soluble dye has been added are added to the detergent solution. With minimal agitation, the entire system appears to take on the color of the dye, due to the dyed oil having been finely dispersed by the spontaneous emulsification effect. This dispersion remains for a considerable length of time, typically 30 minutes to several hours, even when agitation has stopped. By contrast, with surfactant systems which fail to provide spontaneous emulsification, the dyed oil droplets produced during agitation rapidly coalesce to form one or more relatively large oil globules at the air/water interface.

More specifically, this demonstration of spontaneous emulsification can be conducted as follows.

A consumer relevant test soil is dyed with 0.5% Oil Red EGN. A 100 ml sample of the detergent composition being tested is prepared at the desired concentration (typically, about 500 ppm) and temperature in water which is "prehardened" to any desired concentration of calcium ions (typically, about 48 ppm), and contained in an 8 oz. capped jar. The sample pH is adjusted to the intended end-use pH (typically in the range of 6.5 to 10) and 0.2 g of the test soil is added. The jar is shaken 4 times and the sample graded. Alternatively, the sample is placed in a beaker and stirred with a stir bar for 15 seconds. The sample is graded as follows:

0=Clear solution with large red oil droplets in it (0.1–5 mm diameter), i.e., no emulsification;
1=Solution has a definite pink appearance with red oil droplets in it (0.1–1 mm), i.e., slight emulsification;
2=Solution is dark pink with small red droplets in it, i.e., moderate emulsification;
3=Solution is red with small red droplets in it (1–200 mm), i.e., emulsification is substantial;
4=Solution is dark red with little or no visible droplets (<1–50 mm), i.e., emulsification is complete.

Note: The grading can also be done spectrophotometrically (based on light transmittance).

The following embodiments illustrate, but are not limiting of, the present invention.

EXAMPLE I

Step 1: Reductive Amination

Preparation of
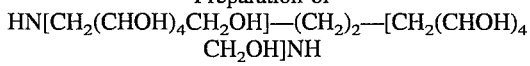

About 375 g (about 20 wt % based on amount of glucose used) of Raney Ni (Grace Raney Nickel 4200) is contained in a 2 gallon reactor (316 stainless steel baffled autoclave with DISPERSIMAX hollow shaft multi-blade impeller) pressurized to about 300 psig with hydrogen at room temperature. The nickel bed is covered with water taking up about 10% of the reactor volume. This is the first reductive amination run on the present load of nickel catalyst.

606.53 g of 50 wt % ethylenediamine solution in water (5.05 moles, 1.00 mole equiv. of ethylenediamine) is maintained in a separate reservoir which is in closed communication with the reactor. The reservoir is pressurized to about 100 psig with nitrogen. 3636.36 g of 55 wt % D-glucose solution in water (11.1 moles, 2.20 mole equiv. of glucose) is maintained in a second separate reservoir which is also in closed communication with the reactor and is also pressurized to about 100 psig with nitrogen.

The ethylenediamine is loaded into the reactor from the reservoir using a high pressure pump. Once all the ethylenediamine is loaded into the reactor, stirring is begun and the reactor heated to 50 deg. C. and pressurized to about 500 psig hydrogen.

The glucose solution is then loaded into the reactor from the reservoir using a high pressure pump similar to the amine pump above. However, the pumping rate on the glucose pump can be varied and on this particular run, it is set to load the glucose in about 10 minutes. Once all the glucose is loaded into the reactor, the pressure is boosted to about 1300 psig hydrogen and the temperature raised to 60 deg. C for about 1 hour. The temperature is then raised to 70 deg. C. for 10 minutes, 80 deg. C. for 10 minutes, 100 deg. C. for 10 minutes, and finally 120 deg. C. for 5 minutes, while maintaining hydrogen pressure between 1300–1500 psig.

The reactor is then cooled to 70 deg. C. and the reaction solution removed from the reactor under hydrogen pressure via an internal dip tube and through a filter in closed communication with the reactor. Filtering under hydrogen pressure allows removal of any nickel particles without nickel dissolution.

Solid product is recovered by evaporation of water. The product purity is approximately 85–90%. Sorbitol is the major impurity at about 10%. The product can be used as is or purified to greater than 99%.

Step 2: Amidation

Preparation of
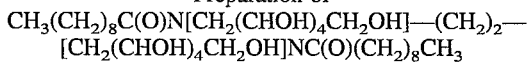

102.13 g of the disugar diamine product of Step 1 (0.263 moles) is dissolved in a solvent mixture of 295.16 g of water and 272.35 g of acetone. With good mixing, 110.32 g of decanoyl chloride (0.578 moles) is slowly added (approx. 1 drop/second) to the disugar diamine solution while simultaneously adding 10 wt % NaOH solution to maintain pH 9–11 throughout the reaction. Once all decanoyl chloride is added, the pH is adjusted to approximately 10 and the reaction is mixed for one hour.

Solid, crude product is obtained by evaporation of water and acetone. The solid, crude product is dissolved in ethanol and the solution filtered to remove NaCl. The filtrate is then concentrated to obtain solid, salt free, crude product. The product purity is approximately 80–90%. The crude product can be used as is.

EXAMPLE II

Step 1: Reductive Amination

Preparation of
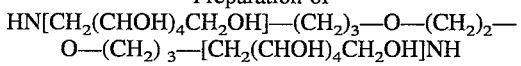

1,2-Bis(3-aminopropoxy)ethane and glucose are reacted in the same manner as Step 1 of Example I for Reductive amination to produce the disugar diamine product.

Step 2: Amidation

Preparation of
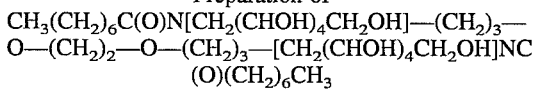

312.12 g of the disugar diamine product of Step 1 (0.618 moles) is melted under nitrogen and then dehydrated under vacuum. With good mixing, 27.35 g of propylene glycol and 234.92 g of methyl octanoate (1.48 moles), which are preheated to 130 deg. C., are added to the melted diamine. Reaction temperature is adjusted to 130 deg. C. and 14.0 g of 25 wt % sodium methoxide (0.0618 moles) solution in methanol is added. Once reaction is homogeneous, the temperature is dropped to 90–100 deg. C. and the reaction methanol is refluxed for 1–2 hours. After refluxing, the methanol is distilled out with the last remaining methanol being pulled out under vacuum for two hours. Reaction is poured out and allowed to cool to room temperature.

The crude product is a viscous liquid with a purity of 70–80% which can be used an is or purified by column chromatography.

EXAMPLES III-VI

Liquid compositions which are especially suitable for "light-duty" use, such as for dishwashing, are prepared having the following ingredients.

| | % By Weight of the Total Composition | | | |
|---|---|---|---|---|
| | III | IV | V | VI |
| C12-C14 alkyl ethoxy sulphate | 9.30 | 9.30 | 15 | 9.30 |
| C12 alkyl N-methyl glucamide | 6.98 | 6.98 | — | 6.98 |
| C12-C14 alkyl carboxylate | 3.48 | 3.48 | — | 3.48 |
| C12-C14 alkyl dimethyl betaine | 1.55 | 1.55 | 2 | 1.55 |
| C12/14 dimethyl amine oxide | 1.16 | 1.16 | 2 | 1.16 |
| C16 dimethyl amine oxide | 3.88 | 7.75 | 5 | — |
| Gemini amide (from Ex. II) | 3.88 | 3.88 | 5 | 7.75 |
| C11 alkyl ethoxylate (ave 9) | 3.48 | 3.48 | 4 | 3.48 |
| Ca++ | 0.14 | 0.14 | 0.15 | 0.14 |
| Mg++ | 0.47 | 0.47 | 0.5 | 0.47 |
| Sodium cumene sulphonate | 3.7 | 3.7 | 3.7 | 3.7 |
| EtOH | 3 | 3 | 3 | 3 |

EXAMPLE VII

A granular detergent composition comprising a non-phosphorus builder system is as follows:

| Ingredient | % (wt.) |
|---|---|
| Oleoyl Sarcosinate, Na | 8.0 |
| Tallowalkyl Sulfate, Na | 2.5 |
| Gemini amide (from Ex. II) | 5.0 |
| $C_{12-14}$ Trimethylammonium Chloride | 1.2 |
| Zeolite A (1-10 micrometer) | 23 |
| Maleic/Acrylic Copolymer | 5.0 |
| Sodium Percarbonate | 12 |
| TAED | 4.0 |
| Sodium Carbonate | 10.6 |
| Sodium Silicate (2.0) | 5.0 |
| Glycerol | 0.5 |
| Savinase (enzyme) | 1.6 |
| Silicone (suds suppressor) | 0.5 |
| Water, Perfume, Minors | Balance |

EXAMPLE VIII

The composition of Example VII is modified by replacing the sodium percarbonate with an equivalent amount of sodium perborate. In an alternate mode, all or part of the TAED bleach activator can be replaced by NOBS bleach activator.

EXAMPLE IX

A granular detergent composition with fabric softening properties comprising a mixed, non-phosphorus builder system is as follows:

| Ingredient | % (wt.) |
|---|---|
| Gemini amide (from Ex. II) | 8.0 |
| $C_{14-15}$ Alkyl Sulfate, Na | 3.0 |
| Sodium Citrate | 5.0 |
| Zeolite A (1-10 micrometer) | 20.0 |
| Sodium Percarbonate | 18.0 |
| TAED/NOBS (1:1) | 5.0 |
| Sodium Sulfate | 12.0 |
| Sodium Silicate | 5.0 |
| $C_{12-14}$ Dimethyl (Hydroxyethyl) Ammonium Chloride | 1.5 |
| Polyacrylate (mw 4000-5000) | 3.0 |
| Hydrogen Tallow Fatty Acid | 0.5 |

-continued

| Ingredient | % (wt.) |
|---|---|
| CAREZYME | 0.9 |
| SAVINASE | 0.75 |
| TERMAMYL | 0.75 |
| Optical Brightener | 0.2 |
| Moisture, Minors | Balance |

EXAMPLE X

In the composition of Example IX, the Zeolite A may be replaced by an equivalent amount of SKS-6. In an alternate mode, the alkyl sulfate can be replaced by a $C_{11-14}$ alkyl benzene sulfonate surfactant and/or by oleoyl sarcosinate surfactant.

EXAMPLE XI

A granular composition comprises the following ingredients.

| Ingredient | % (wt.) |
|---|---|
| Gemini amide (from Ex. II) | 19.0 |
| Zeolite A (1-10 microns) | 25.0 |
| Sodium Citrate | 3.0 |
| Sodium Percarbonate | 12.0 |
| Polyaspartate | 5.0 |
| EDDS | 3.0 |
| Protease | 1.0 |
| Lipase | 1.0 |
| TAED | 5.0 |
| Sodium Carbonate | 10.0 |
| Sodium Silicate | 3.0 |
| Water and Minors | Balance |

EXAMPLE XII

The composition of Example XI is modified by reducing the Gemini amide to 17% of the composition and adding 2% by weight of coconutalkyl ethoxylate (1-5 avg. ethoxylate) as NEODOL.

EXAMPLE XIII

A detergent bar is prepared by compacting and extruding a composition generally according to Example XI. Where allowed by statute, the zeolite/citrate builder may be replaced by a phosphate builder such as sodium tripolyphosphate.

EXAMPLE XIV

These granular detergents can be prepared by spray-drying (final product density 520 g/l) or agglomerating (final product density above 600 g/l) the Base Granule. The remaining dry ingredients are admixed in granular or powder form with the Base Granule in a rotary mixing drum, and the liquid ingredients (nonionic lo surfactant and perfume) are sprayed on.

| | A | B | C |
|---|---|---|---|
| Base Granule | | | |
| $C_{14-15}$ alkyl sulfate | 5.8 | — | — |
| Gemini amide (from Ex. II) | 6.0 | 11.0 | 6.0 |
| $C_{16-18}$ fatty acid | 2.2 | — | 2.2 |
| Zeolite A (1-10 microns) | 7.0 | 7.0 | 7.0 |

27
-continued

|  | A | B | C |
|---|---|---|---|
| Polyacrylate (4500 MW) | 3.3 | 3.3 | 3.3 |
| Polyethylene glycol (8000 MW) | 1.3 | 1.3 | 1.3 |
| Sodium carbonate | 10.7 | 10.7 | 10.7 |
| Sodium sulfate | 5.0 | 5.0 | 5.0 |
| Sodium silicate ($SiO_2/Na_2O = 2$) | 5.0 | 5.0 | 5.0 |
| Miscellaneous | 7.1 | 7.1 | 7.1 |
| Admix |  |  |  |
| Zeolite A (1–10 micron) | 5.0 | 5.0 | 5.0 |
| $C_{12-18}$-N-(3-methoxypropyl) glucamide | — | 6.4 | — |
| $C_{12-14}$N-methyl glucamide | 4.0 | — | 4.4 |
| $C_{14-15}$ alkyl sulfate | 11.8 | — | — |
| $C_{12-18}$ alkyl ethoxy (2) sulfate | — | — | 5.0 |
| $C_{14-15}$ alkyl ethoxy (2.25) sulfate | 4.0 | — | — |
| Suds suppressor flake* | — | 1.0 | 0.5 |
| Miscellaneous (filler salts, brightener, enzyme, buffer, zeolite or other builder, etc) | 17.2 | 17.2 | 16.5 |
| Spray-on |  |  |  |
| $C_{12-13}$ alkyl ethoxylate (6.5 EO) | 2.0 | 2.0 | 2.0 |
| Perfume | 0.5 | 0.5 | 0.5 |
| Water and miscellaneous | Balance | | |

*Suds Suppressor Flake contains approximately 5% of a silica/silicone oil dispersion encapsulated in a flake containing primarily PEG (8000 MW), at greater than 80%, and minor optional water soluble ingredients.

The compositions of this example may be modified to form a bleach-containing composition by adding sodium percarbonate (in an amount to provide 12 weight percent) and TAED bleach activator (in an amount to provide 4 weight percent). Also, the TAED may be replaced by NOBS bleach activator.

EXAMPLE XV

The composition of Example XIV(A) is modified by the addition of 0.2% (based on final product) CAREZYME (cellulase) in the admix. Alternatively, a 1:1:1 mixture of LIPOLASE (lipase), cellulase and protease at a total weight % of product of 0.9% can be added via the admix.

EXAMPLE XVI

The composition of Example XIV(B) is modified by the addition of 10% sodium percarbonate (100–500 micron) or sodium perborate monohydrate and 1% tetraacetylethylenediamine or 1% nonanoyloxybenzene sulfonate (based on final product) via the admix to provide a bleaching function.

EXAMPLE XVII

A liquid laundry detergent composition herein comprises the following.

| Ingredient | % (wt.) |
|---|---|
| Oleoyl sarcosinate, Na | 15.0 |
| Gemini amide (from Ex. II) | 5.0 |
| Sodium citrate | 3.0 |
| $C_{10}$ alcohol ethoxylate (3) | 13.0 |
| Monoethanolamine | 2.5 |
| MAXATASE (enzyme) | 0.5 |
| LIPOLASE (enzyme) | 0.5 |
| $CaCl_2$ | 0.1 |
| Water/propylene glycol/ethanol (100:1:1) | Balance |

EXAMPLE XVIII

Highly concentrated liquid laundry detergents are as follows.

| Ingredient | % (wt.) |
|---|---|
| Oleoyl sarcosinate, Na* | 15.0 |
| $C_{14-15}$ EO (2.25) sulfate, Na | 15.0 |
| Gemini amide (from Ex. II) | 10.40 |
| Citric acid | 5.0 |
| $C_{12-14}$ fatty acid | 4.00 |
| Ethoxylated tetraethylene pentamine | 0.99 |
| Boric acid | 2.00 |
| NaOH | 3.79 |
| 1,2-propanediol | 9.15 |
| Ethanol | 6.55 |
| Monoethanolamine | 1.05 |
| Sodium cumene sulfonate | 3.96 |
| $H_2O$/minors | Balance |
| pH 10% aq. solution | 8.29 |

*Potassium, ammonium or triethanolammonium salts may also be used.

What is claimed is:

1. Novel gemini polyhydroxy fatty acid amide compounds having the formula:

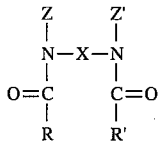

wherein:

X is selected from the group consisting of unsubstituted, linear alkyl moieties having the formula $-(CH_2)_n-$, wherein n is an integer from 2 to about 15, and unsubstituted, branched alkyl moieties having from 2 to about 15 carbon atoms; Z and Z' are independently selected from the group consisting of $-CH_2-(CHOH)_p-CH_2OH$, $-CH(CH_2OH)-(CHOH)_{p-1}-CH_2OH$, $-CH_2-(CHOH)_2(CHOR^1)(CHOH)-CH_2OH$, where p is an integer from 1 to 5, inclusive, and $R^1$ is H or a cyclic mono- or polysaccharide, and alkoxylated derivatives thereof, or one of Z or Z' is hydrogen; and R and R' are the same or different hydrocarbyl moieties having from about 1 to about 21 carbon atoms and can be saturated, branched or unsaturated and mixtures thereof.

2. A compound according to claim 1 wherein R and R' are independently selected from the group consisting of straight or branched chain $C_3-C_{13}$ alkyl or alkenyl moieties.

3. A compound according to claim 1 wherein X is selected from the group consisting of $-(CH_2)_2-$, $-(CH_2)_3-$, $-(CH_2)_4-$, $-(CH_2)_5-$, $-(CH_2)_6-$, $-CH_2CH(CH_3)(CH_2)_3-$; Z and Z' are independently selected from the group consisting of $-CH_2-(CHOH)_4-CH_2OH$; and R and R' are independently selected from the group consisting of straight chain $C_5-C_{11}$ alkyl or alkenyl moieties.

4. Compositions comprising:
   (a) at least about 0.1% of a gemini polyhydroxy fatty acid amide compound according to claim 1; and
   (b) at least about 0.1% of one or more laundry or personal care composition materials.

5. Compositions comprising:
   (a) at least about 0.1% of a gemini polyhydroxy fatty acid amide compound according to claim 2; and
   (b) at least about 0.1% of one or more laundry or personal care composition materials.

6. Compositions comprising:
(a) at least about 0.1% of a gemini polyhydroxy fatty acid amide compound according to claim 4; and
(b) at least about 0.1% of one or more laundry or personal care composition materials.

7. A method for laundering fabrics or cleaning hard surfaces, comprising contacting said fabrics or hard surfaces with an aqueous solution containing at least about 10 ppm of a gemini polyhydroxy fatty acid amide surfactant according to claim 1.

8. A method for laundering fabrics or cleaning hard surfaces, comprising contacting said fabrics or hard surfaces with an aqueous solution containing at least about 10 ppm of a gemini polyhydroxy fatty acid amide surfactant according to claim 2.

9. A method for laundering fabrics or cleaning hard surfaces, comprising contacting said fabrics or hard surfaces with an aqueous solution containing at least about 10 ppm of a gemini polyhydroxy fatty acid amide surfactant according to claim 3.

* * * * *